(12) United States Patent
Ponzi et al.

(10) Patent No.: US 7,776,017 B2
(45) Date of Patent: Aug. 17, 2010

(54) CATHETER CLAMP

(75) Inventors: Dean M. Ponzi, Glendora, CA (US); Benjamin D. McDaniel, Corona Del Mar, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1224 days.

(21) Appl. No.: 10/940,407

(22) Filed: Sep. 14, 2004

(65) Prior Publication Data

US 2006/0058738 A1 Mar. 16, 2006

(51) Int. Cl.
*A61M 5/32* (2006.01)

(52) U.S. Cl. ...................................... 604/180

(58) Field of Classification Search ................. 604/250, 604/174, 178, 179, 180, 903; 128/277, DIG. 26
See application file for complete search history.

(56) References Cited

U.S. PATENT DOCUMENTS

| 2,471,623 | A | * | 5/1949 | Hubbell ................. 137/625.18 |
| 3,487,837 | A | | 1/1970 | Petersen |
| 3,821,957 | A | | 7/1974 | Riely et al. |
| 4,697,785 | A | * | 10/1987 | Tuseth ........................... 251/9 |
| 4,985,018 | A | | 1/1991 | Smith |
| 5,098,392 | A | | 3/1992 | Fleischhacker et al. |
| 5,127,626 | A | | 7/1992 | Hilal et al. |
| 5,364,367 | A | | 11/1994 | Banks et al. |
| 5,437,645 | A | | 8/1995 | Urban et al. |
| 5,653,700 | A | | 8/1997 | Byrne et al. |
| 5,690,616 | A | | 11/1997 | Mogg |
| 5,755,225 | A | | 5/1998 | Hutson et al. |
| 5,792,112 | A | | 8/1998 | Hart et al. |
| 5,836,914 | A | | 11/1998 | Houghton |
| 5,979,840 | A | * | 11/1999 | Hollister et al. ................ 248/76 |
| 6,488,664 | B1 | | 12/2002 | Solomon et al. |
| 6,572,588 | B1 | * | 6/2003 | Bierman et al. .............. 604/180 |
| 6,589,262 | B1 | | 7/2003 | Honebrink et al. |
| 6,951,550 | B2 | * | 10/2005 | Bierman ...................... 604/174 |
| 2004/0162544 | A1 | | 8/2004 | Raulerson et al. |

OTHER PUBLICATIONS

International Search Report dated Dec. 27, 2005 for correspondhg Appln. No. PCT/US2005/033059.

* cited by examiner

*Primary Examiner*—Manuel A Mendez
(74) *Attorney, Agent, or Firm*—Christie, Parker & Hale, LLP (57) ABSTRACT

The present invention is directed to a catheter clamp that is affixable to a patient's skin to hold a catheter in position while in use within a patient's body. In one embodiment, the clamp has a base adapted to be removably adhered to the patient's skin, two clamp members supported on the base and defining a region therebetween to receive the catheter body, the clamp members being adapted to move between an open position and a closed position, and locking means for releasably locking said clamp members in said closed position to hold the catheter body in a generally fixed position relative to said clamp. In another embodiment, the clamp includes a base adapted to be removably adhered to the patient's skin, two clamp members supported on the base and defining a space therebetween to receive the catheter body, the clamp members being adapted to move between an open position and a closed position, and an elongated release tab extending between the two clamp members and configured to releasably lock the clamp member around the catheter body. The two clamp members may be pivotably coupled to each other and the tab may be pivotably attached on one of the clamp members.

17 Claims, 5 Drawing Sheets

CATHETER CLAMP

FIELD OF INVENTION

This invention relates to catheters and catheter accessories, particularly, devices that hold a catheter stationary and in position while in use in a patient's body.

BACKGROUND OF THE INVENTION

Electrode catheters have been in common use in medical practice for many years. They are used to stimulate and map electrical activity in the heart and to ablate sites of aberrant electrical activity. In use, an electrode catheter is inserted into a major vein or artery, e.g., femoral artery, and then guided into the chamber of the heart which is of concern. The catheter should preferably be deflectable to permit proper positioning of the electrodes on its distal end within the heart.

Deflectable tip electrode catheters are well known. Such a catheter generally has a control handle at its proximal end for controlling deflection of the tip in one or more directions. For example, a particularly useful deflectable tip catheter is disclosed in U.S. Pat. No. Re. 34,502 to Webster, the disclosure of which is hereby incorporated by reference. This catheter comprises a puller wire that extends on-axis through an elongated reinforced catheter body and then off-axis in a deflectable tip portion. In this arrangement, longitudinal movement of the puller wire relative to the catheter body results in deflection of the catheter tip portion. Other examples of steerable catheters can be found in U.S. Pat. No. 5,431,168 to Webster entitled "Steerable Open-Lumen Catheter" and U.S. patent application Ser. No. 08/924,611 to Webster entitled "Omni-Directional Steerable Catheter," the disclosures of which are hereby incorporated by reference.

One drawback to catheters and perhaps especially deflectable catheters is their tendency to shift from a treatment site in a patient's body when the catheter is released from a user's grip. Typically, when using a catheter the physician has to maintain his hold on the catheter in order to maintain the catheter's position in the patient's body. If the physician releases his hold, a suitable tissue site which has been located for treatment or evaluation, such as mapping, ablation or the like, can be easily lost with the slightest movement of the catheter. As such, the physician is often hampered by the need to maintain a hand on the catheter body during the course of the medical procedure. The problem may be greater with deflectable catheters which can store torsional energy and therefore readily unwind and shift when released from the doctor's grasp. With the heart chamber being a dynamic environment surrounded by moving tissue and blood flow, the ability to maintain the position of the catheter at the target site in a hands-free manner is most desirable.

Often with one hand already working the introducer or sheath, the physician may desire the ability to use that same hand to operate the catheter clamp. Moreover, it would therefore be desirable to bias the clamp toward a closed position so that clamping the catheter involves minimal action on behalf of the physician.

SUMMARY OF THE INVENTION

The present invention is directed to a catheter clamp that is affixable to a patient's skin to hold a catheter in position while in use within a patient's body. In one embodiment, the clamp has a base adapted to be removably adhered to the patient's skin, two clamp members supported on the base and defining a region therebetween to receive the catheter body, the clamp members being adapted to move between an open position and a closed position, and locking means for releasably locking said clamp members in said closed position to hold the catheter body in a generally fixed position relative to said clamp. The clamp may also have a bias member biasing at least one of said clamp members toward the closed position and/or a bias member biasing at least one of said clamp members toward the open position. Moreover, the locking means can include a tab movable between a release position and a locking position, where the tab extends between said clamp members. The locking means may also include a second bias member adapted to bias the tab toward the locking position. In a detailed embodiment, the clamp members are U shaped or C shaped and the tab can be configured to prop open a clamp member.

In another embodiment, the clamp includes a base adapted to be removably adhered to the patient's skin, two clamp members supported on the base and defining a space therebetween to receive the catheter body, the clamp members being adapted to move between an open position and a closed position, and an elongated release tab extending between the two clamp members and configured to releasably lock the clamp member around the catheter body. The two clamp members may be pivotably coupled to each other and the tab may be pivotably attached on one of the clamp members. Furthermore, the tab may have a profile configured to prop open the clamp members, and the clamp may include a bias member to bias the clamp members toward the open position. In addition, the clamp may have a bias member to bias tab toward a release position.

In yet another embodiment, the clamp has a base adapted to be removably adhered to the patient's skin, two clamp members supported on the base where the clamp members define a passageway for receiving the catheter body and are adapted to move between an open position and a closed position, a cam supported on the base and configured to move at least one of the clamp members into the closed position, and a lever adapted to enable a user to control movement of the cam. The clamp may have an adhesive coating on a bottom surface of the base to enable the clamp to be removably adhered to the patient. The clamp may also have a bias member that biases one of the clamp members to move into the open position. In a detailed embodiment, one clamp member can be stationary relative to the base while the other clamp member is movable relative to the base.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
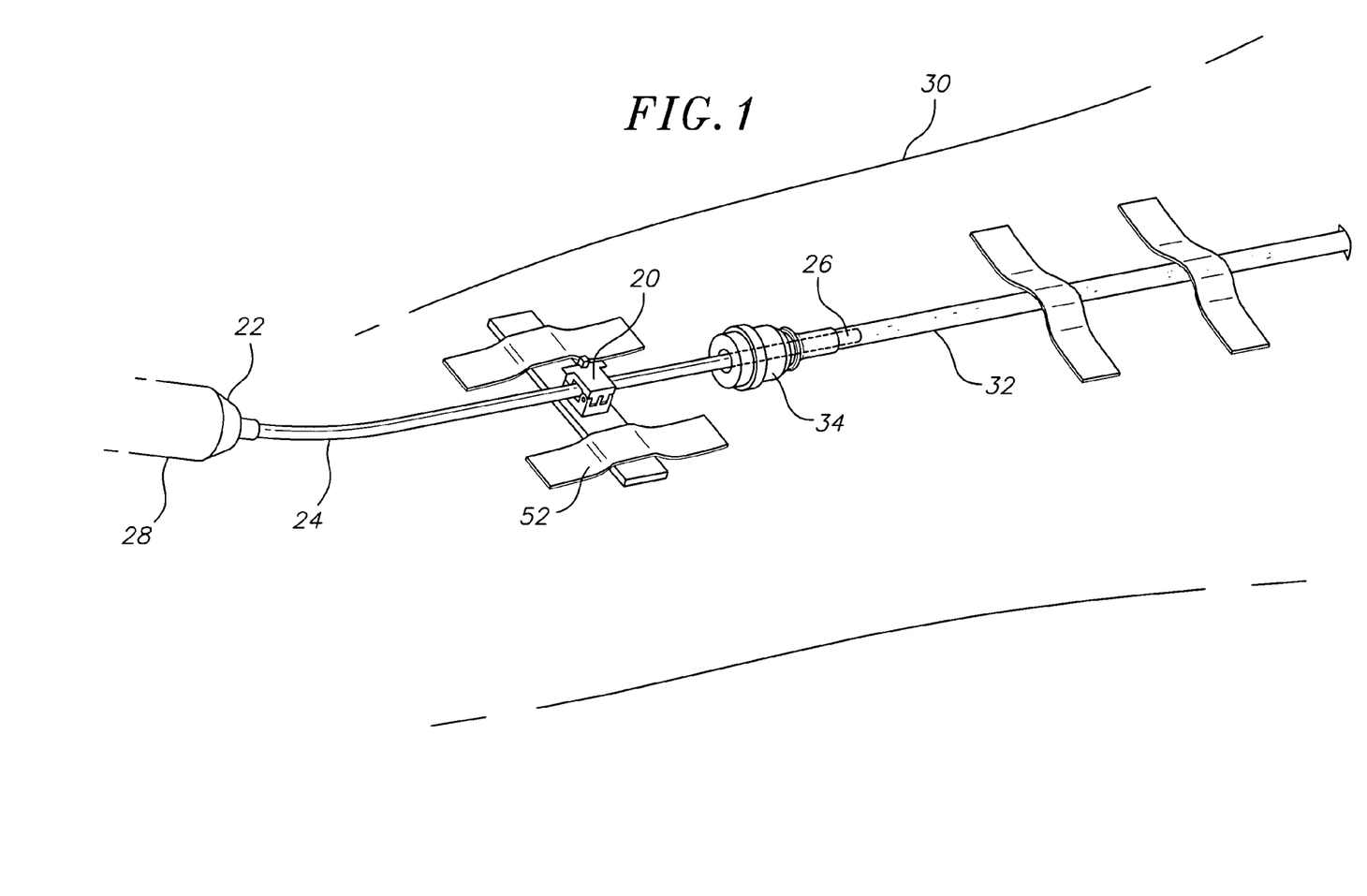
FIG. 1 is a perspective view of an embodiment of a catheter clamp of the present invention in use on a patient's body with an introducer (or sheath) and a catheter.

FIG. 1 illustrates a catheter clamp 20 in accordance with an embodiment of the present invention. For purposes of the discussion herein, a catheter 22 suitable for use with the clamp includes a catheter body 24 that typically extends between a catheter tip 26 and a control handle 28. The catheter body 24 and the catheter tip 26 are portions that can enter a patient's body typically via a leg 30; the catheter control handle however remains outside the patient's body.

The clamp 20 is adapted to releasably hold a catheter 22 in position while in use in the patient's body during treatment or evaluation, such as mapping, ablation and the like. Once closed, the clamp 20 holds the catheter body (along with parts of the catheter distal the catheter body) in a generally stationary position in the patient's body and effectively minimizes, if not prevents, linear or rotational movement that may cause the catheter tip to shift from the treatment site. In particular, the clamp 20 when closed frees both hands of the attending doctor to conduct other activities and can be released so that the catheter can be repositioned, as needed, during the course of the medical procedure. Advantageously, the catheter clamp 20 does not interfere with the use of an introducer or sheath 32 having a valve 34, e.g., a hemostasis valve, that is inserted into a patient's vein or artery. As is well known, the introducer 32 facilitates the entry of a catheter into the vein and ultimately the heart by providing a portal into the patient's body.

Referring to FIGS. 2-6, one embodiment of the clamp 20 has two opposing members 40 and 42 supported on an upper surface 44 of a base 46. The base has a lower surface 48 that is covered with an adhesive or adhesive coating 50 so that the clamp can be removably affixed to the patient's skin. The base 46 can have any configuration or size as appropriate to enable the clamp 20 to securely hold the catheter in position once the catheter body is locked in the clamp. In fact, the base 46 may extend a distance x laterally beyond one or both sides of the opposing members 40 and 42 so that the clamp can be further secured to the patient's skin with medical tape and/or bandage 52 (FIG. 1). A removable liner 54 may be provided to cover the adhesive until the clamp is ready to be affixed to the patient. It is understood by one of ordinary skill in the art that the clamp 20 may be affixed to the patient at any distance from the introducer 32 so long as the clamp can securely hold the catheter 22 and minimize at least the portion of the catheter body held in the clamp from moving rotationally, distally and/or proximally once the clamp is closed and the catheter body 24 is released from the physician's hold.

Figure 4:
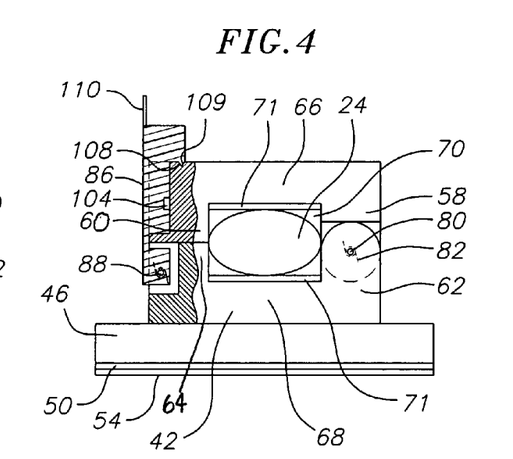
FIG. 4 is a side view of the catheter clamp of FIG. 2 in the closed position.
Figure 5:
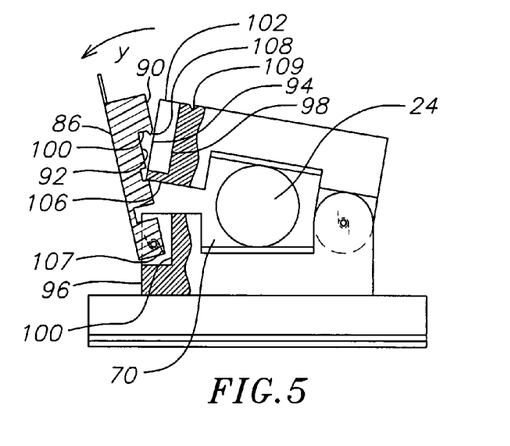
FIG. 5 is another side view of the catheter clamp of FIG. 2 in the open position.
Figure 6:
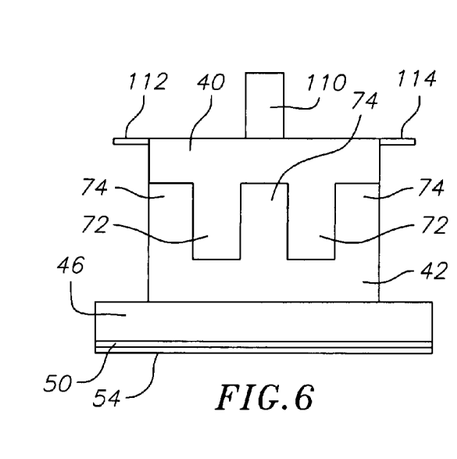
FIG. 6 is a rear view of the catheter grip of FIG. 2.

As best seen in FIGS. 4 and 5, each of the two opposing members 40 and 42 is configured with a U or C shaped cross-section that have legs 58, 60, 62 and 64 extending from a main portion 66 and 68. The opposing members 40 and 42 are stacked on top of one another (such that one can be generally designated as the top member 40 and the other generally as the bottom member 42) and facing each other such that the legs 58 and 62 and the legs 60 and 64 can meet and along with the main portions 66 and 68 define a passage way 70 therebetween. In this embodiment, the bottom member 42 is stationery relative to the base 46 while the top member 40 is movable relative to the base 46. A friction-inducing coating or lining 71 can line the passage way 70 to improve the hold of the clamp on the catheter body 24.

The members 40 and 42 are pivotably connected to each other by means of a pivot connection which, in one embodiment, includes hinge means or hinge portion 72 and 74 that are formed in the legs 58 and 62 and pivotably coupled to each other by a pin 80. As such, the clamp 20 is movable between a closed or locked position (FIG. 4) and an open or release position (FIG. 5). A bias means such as a spring leaf 82 may be placed in the hinge portions 72 and 74 near or around the pin 80 to bias the members 40 and 42 to urge the clamp 20 to close.

In the closed position, the clamp securely holds the catheter body 24 within the passageway 70. As understood by one of ordinary skill in the art, depending on the diameter and/or flexibility of the catheter body, the passage way 70 is sized such that the catheter body 24 is sufficiently compressed between the top and bottom members 40 and 42 to generally prevent rotational and/or translational movement of the catheter body within the passageway relative to the clamp. However, where the catheter body has lumen(s) extending along its length, it may be desirable in certain instances to provide a level of compression that holds the catheter body but does not hamper flow or communication in the lumen, for example, the passage of fluid to or from the treatment site.

The clamp 20 should be constructed of a suitably rigid material (including plastic, steel, stiff rubber, and the like, or combinations or subcombinations thereof). The clamp should preferably be sufficiently rigid to hold the portion of catheter body held and parts distal thereof in position once the catheter body 24 has been clamped in the clamp 20.

Figure 2:
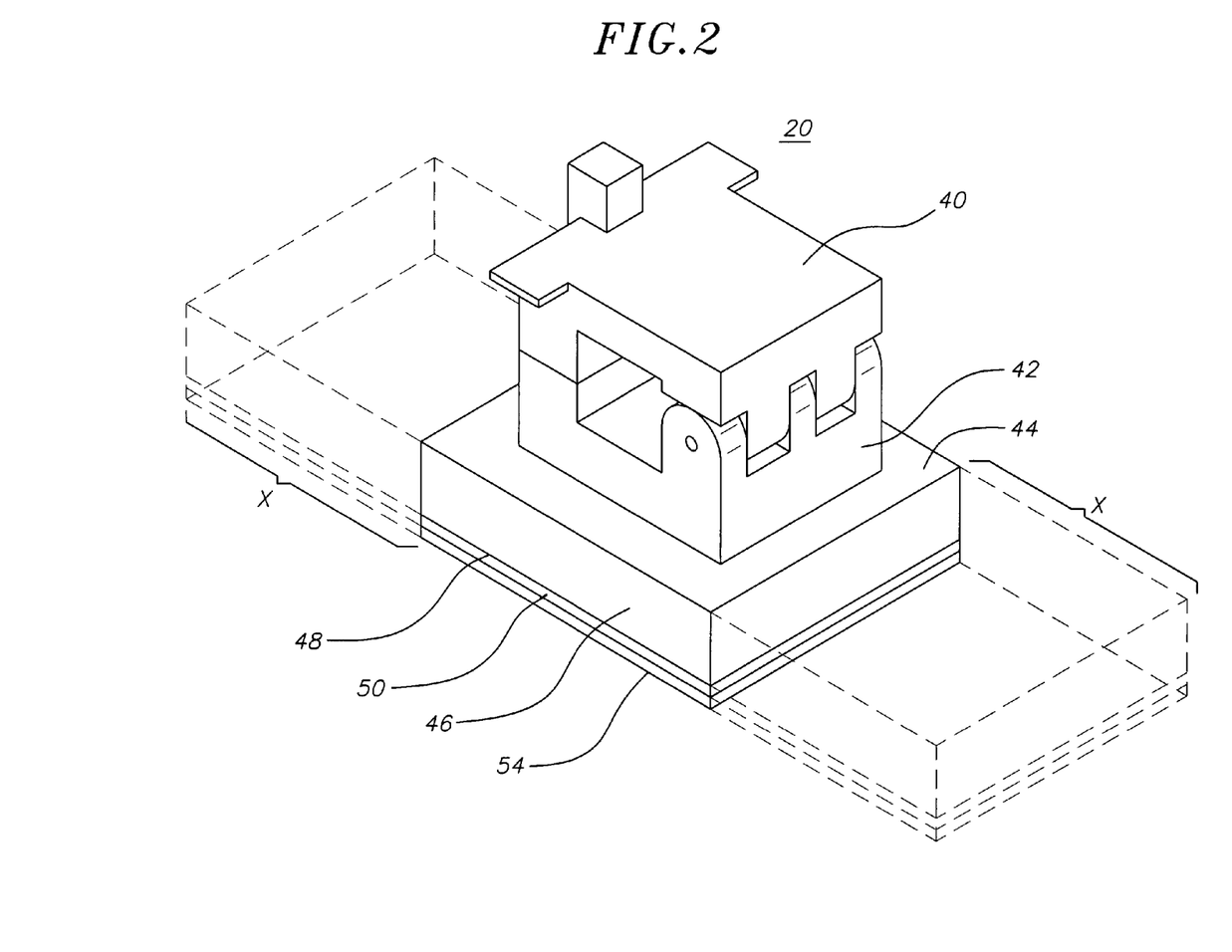
FIG. 2 is a perspective view of an embodiment of a catheter clamp of the present invention in the closed position.
Figure 3:
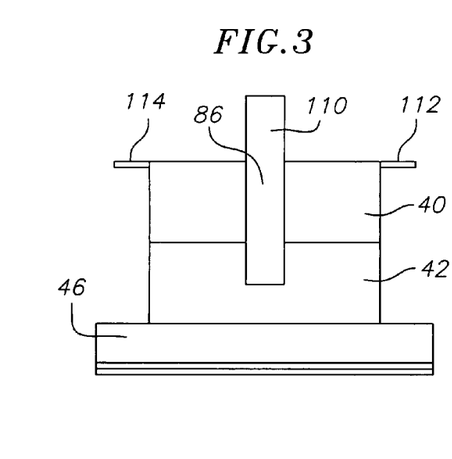
FIG. 3 is a front view of the catheter clamp of FIG. 2.

As also shown in FIGS. 2-4, a release tab 86 is provided extending across the legs 60 and 64 and opposing the pivot portions 72 and 74 from across the passageway 70. The release tab 86 being an elongated member is adapted to pivot about an axis 88 toward and away from the top and bottom members 40 and 42 as shown by the arrow Y and is situated to extend between the legs 60 and 64 to releasably lock the top and bottom members 40 and 42 to each other. In the illustrated embodiment, the release tab is pivotably mounted in leg 64 of the bottom member 42 to extend generally vertically therefrom.

A profile 90 is provided on a face 92 facing the top and bottom members 40 and 42, each of which also has a face 94 and 96 with a profile 94 and 96 that corresponds with its respective portion of the tab profile 90. In that regard, the profile 90 in one embodiment includes a lip 100 that is adapted to catch an upper edge 102 of the top member 40 when the clamp is closed and also a recess 104 that is adapted to catch a lower edge 106 of the top member 40 when the clamp is open. In particular, when the clamp 20 is closed, the lip 100 overhangs the upper edge 102 thereby locking the top member 40 to the bottom member 42 (FIG. 4), and when the clamp 20 is open, the recess 104 maintains the clamp 20 open or at least ajar (FIG. 5). To that end, the tab 86 is biased by a biasing means, e.g., leaf spring 107, to pivot toward the top and bottom members 40 and 42, thereby facilitating the engagement of the lip 100 with the upper edge 102 or the engagement of the recess 104 with the lower edge 106. The lip 100 may have a catch 108 that catches a recess 109 near the upper edge 102.

The release tab 86 also has a flange 110 by which the physician or user can trip the tab 86 open with relative ease to unlock the clamp 20. Moreover, extending laterally beyond the top member 40 are flanges 112 and 114 (FIGS. 3 and 6) by which the user can flick or lift open the clamp 20 once the tab 86 has been released.

Accordingly, referring to FIGS. 1-6, when in use, the clamp 20 may be affixed to the patient's skin at any location but preferably adjacent any introducer or sheath being used or the portal into the patient's body. The liner 54 may be removed to expose the adhesive coating 50 and medical tape 52 may be used to further secure the clamp 20 to the patient's skin.

In order to receive the catheter body 24 (typically but not limited to before the catheter tip 26 and catheter body 24 enter the patient's body), the clamp is unlocked by means of the tab 86 which is pivoted away from the members 40 and 42 by the user pushing outwardly on the flange 110. The catheter body 24 is placed in the passageway 70 and fed into the patient's body (if not already) and advanced distally until the treatment site is reached. To lock the clamp 20 to the catheter body 24, the physician presses down on the top member 40 to close the clamp and moves the release tab 86 inwardly toward the members 40 and 42 until the lip 100 engages the edge 102 of the top member 40 and the catch 108 catches the recess 109. The compression exerted by the top and bottom members 40 and 42 securely holds the portion of the catheter body 24 extending through the passage way 70 which should in turn hold in position at least the catheter body and tip distal thereof, if not also a portion of the catheter body proximal thereof. As such, the physician is free to release his or her grip on the catheter body and to move about the room or perform any other tasks with one or both of his or her hands.

In the event the position catheter tip and/or body needs readjusting or the catheter tip needs to be moved to a different treatment site in the patient's body, the physician can flick open the release tab 86 against the bias of the spring 106 and then manipulate the flanges 110, 112 and/or 114 until the lower edge 106 of the top member 40 rests in the recess 104 of the tab 86 which props the clamp ajar while he/she adjusts the position of the catheter body as needed. When the appropriate adjustment has been made, the physician can relock the clamp 20 by flicking open the tab 86 and closing the top member 40 onto the bottom member 42 under the bias of the spring 82 and again locking the lip 100 of the tab 86 over the edge 102.

It is understood by one of ordinary skill in the art that the members 40 and 42 need not be stacked one on top of another and that either or both of the members 40 and 42 can be movable relative to each other and/or the base. In particular, the members 40 and 42 can be oriented such that the main portions 66 and 68 extend generally upwardly/vertically (as opposed to generally horizontally) and are both movable between an open position and a closed position, with the hinge portions 72 and 74 positioned in and/or extending generally upwardly from the base.

Figure 7:
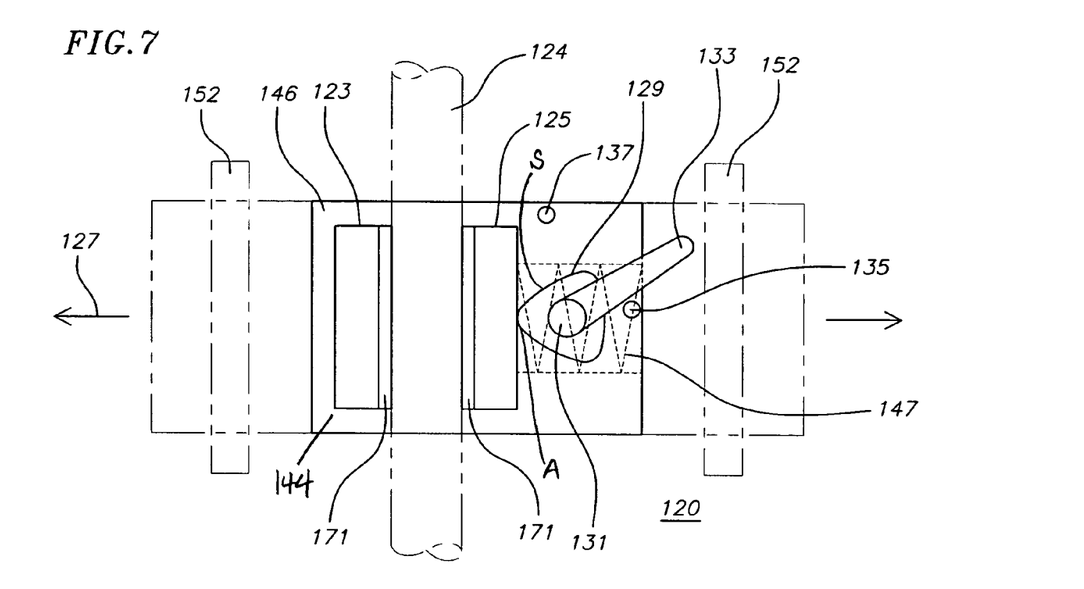
FIG. 7 is a top plan view of an alternative embodiment of a catheter clamp in accordance with the present invention in use with a catheter, in the open position.

In yet another embodiment, a catheter clamp 120 as shown in FIGS. 7-11, has a base 146, an adhesive coating 150 and a liner 154 which allow the clamp to be affixed to a patient's skin. As described above, the base 146 may be of any dimension or configuration so long as it enables the clamp to be securely affixed to the patient by means of the adhesive coating 150 and/or medical tape 152 (FIG. 7). Fixedly mounted onto an upper surface 144 of the base is a stationary member 123 which extends generally vertically from the base 146 to a height that is generally greater than the diameter of a catheter body 124. A contacting surface of the member 123 may be covered with a friction-inducing lining 171 to improve the hold of the clamp on the catheter body 124.

Opposing the stationery member 123 from across a passageway 170 for the catheter body 124 is a movable member 125 of a similar configuration that is slidable toward and away from the member 123 along an axis 127 generally perpendicular to a longitudinal axis of the catheter body 124 sitting in the clamp. A lining 171 may also cover a contacting surface of the member 123 to improve the hold of the clamp on the catheter body.

Positioned to act on the movable member 125 is a cam 129 that is pivotable about a pin 131 by means of a handle or toggle lever 133 that is movable by the user between a closed or lock position (FIGS. 8 and 10) and an open or release position (FIGS. 7 and 9) as limited by the stops 135 and 137 extending generally upwardly from the base 146. In the illustrated embodiment, the cam 129 has a generally triangular cross-section with apex A and a side S, but it is understood by one of ordinary skill in the art that the cam 129 can be configured differently if different movement of the member 125 is desired. Depending on the position of the toggle lever 133, either the apex A is engaged with the member 125 to move it toward the member 123, or the side S faces the member 125 enabling it to move away from the member 123 under a bias force of a bias means, for example, a coil spring 147 drawing the member 125. It is understood by one of ordinary skill in the art that the cavity 141 and the coil 147 can be arranged in the base 146 such that the coil instead pushes the member 125 away from the member 123.

Figure 8:
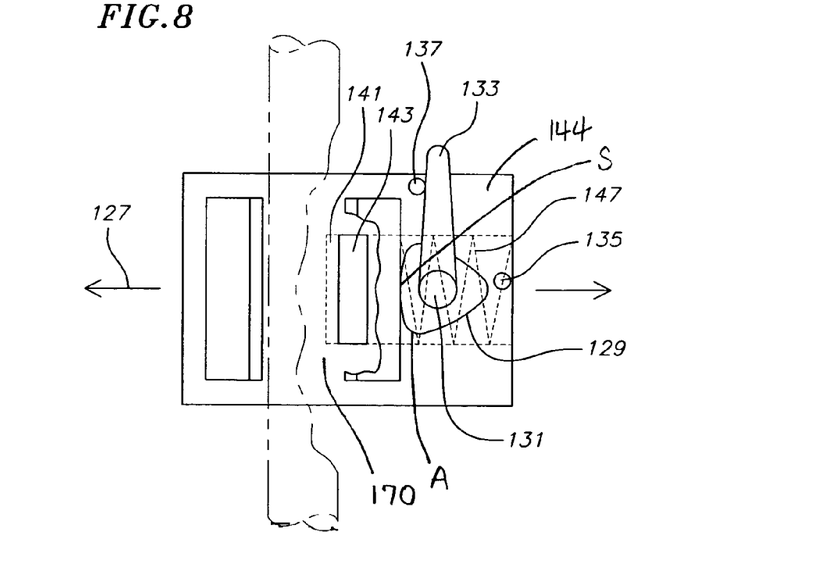
FIG. 8 is the catheter clamp of FIG. 7 in the closed position, with pieces broken away to show an aperture and a cavity in a base.
Figure 9:
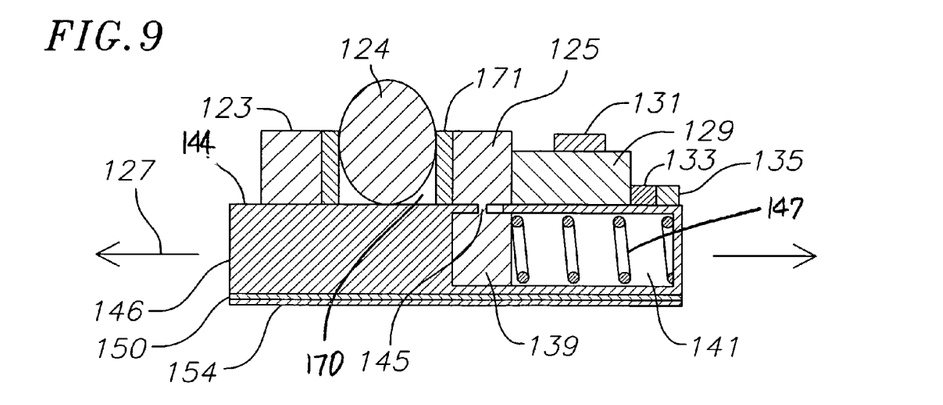
FIG. 9 is a cross sectional view of the catheter clamp of FIG. 7 taken along axis 127.
Figure 10:
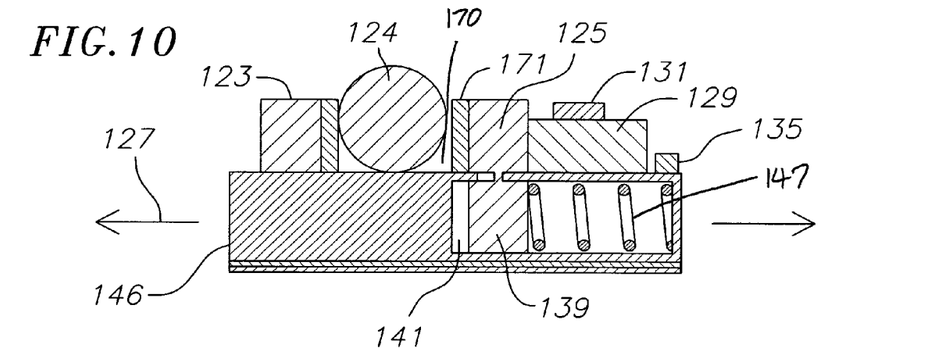
FIG. 10 is a cross-sectional view of the catheter clamp of FIG. 8 taken along axis 127.
Figure 11:
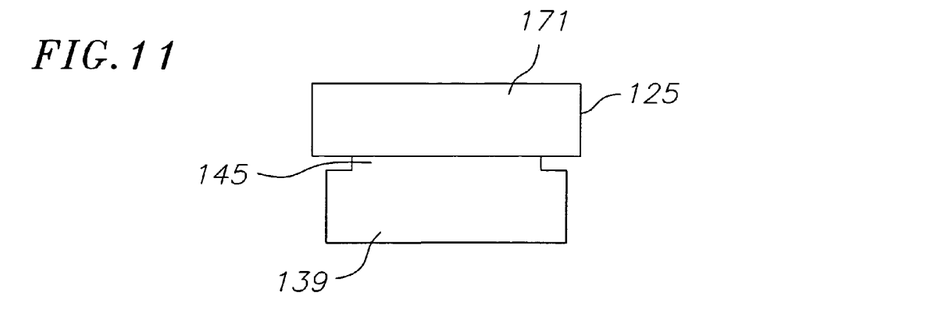
FIG. 11 is a front view of a movable clamp member of the clamp of FIG. 7.

As better shown in FIGS. 8-10, the movable member 125 is configured with a base portion 139 that extends into the base 146 which is configured with a cavity 141 accessible through an aperture 143 formed in the upper surface 144. The aperture is configured large enough to accommodate a connecting portion 145 of the member 125 and permit translational movement of the member 125 along the axis 127 so as to open (FIG. 10) and close (FIG. 10) the clamp. The aperture 143 is also configured small enough that the base portion 139 remains in the cavity 141. The cavity 141 is configured to accommodate the translational movement of the base portion 139 and also the coil spring 147, to bias the member 125. In the illustrated embodiment, the connecting portion 145 sits in the aperture 143 such that the base portion remains in the cavity and the member 125 is urged away from the member 123 by the spring 147.

In use, the clamp 120 may be affixed to the patient's skin at any location but preferably adjacent any introducer or sheath being used or the portal into the patient's body. The liner 154 may be removed to expose the adhesive coating 150 and medical tape 152 may be used to further secure the clamp 120 to the patient's skin.

In order to receive the catheter body 124 (typically but not limited to before the catheter tip 26 and catheter body 124 enter the patient's body), the clamp is opened by the user by means of the toggle lever 133 which is pivoted by the user from the stop 135 to the stop 133. The cam 129 in turn is rotated such that the apex A rotates away from the member 125 and the side S allows the member 125 to open under the bias of the spring 147. The catheter body 124 is placed in the passageway 170 and fed into the patient's body (if not already) and advanced distally until the treatment site is reached. To lock the clamp 120 to the catheter body 124, the physician moves the toggle lever 133 from the stop 137 to the stop 135 which rotates the apex A of the cam 129 back into contact with the member 125 and moves the member 125 toward the member 123. This movement compresses the catheter body in the passageway 170 between the members 123 and 125 and results in a secure hold by the clamp 120 of the portion of the catheter body 124 extending through the passage way 70 which should in turn hold in position at least the catheter body and tip distal thereof, if not also a portion of the catheter body proximal thereof. As such, the physician is free to release his or her grip on the catheter body and to move about the room or perform any other tasks with one or both of his or her hands.

In the event the position catheter tip and/or body needs readjusting or the catheter tip needs to be moved to a different treatment site in the patient's body, the physician rotates the toggle lever 133 from the stop 135 to the stop 137 which enables him to adjust the position of the catheter body as needed. When the appropriate adjustment has been made, the physician can relock the clamp 120 by returning the toggle lever 133 from the stop 137 to the stop 135.

It is understood by one of ordinary skill in the art that either or both of the members 40 and 42 can be movable relative to each other and/or the base.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter clamp for use with a catheter positionable in a patient, the catheter having a catheter body, the clamp comprising:
    a base adapted to be removably adhered to the patient's skin;
    two clamp members supported on the base and defining a region therebetween to receive the catheter body, the clamp members adapted to move between an open position and a closed position;
    locking means for releasably locking said clamp members in said closed position to hold the catheter body in a generally fixed position relative to said clamp, wherein the locking means is configured to pivot about an axis toward and away from the two clamp members; and
    a bias member biasing the locking means toward the two clamp members.

2. A catheter clamp of claim 1, further comprising a second bias member biasing at least one of said clamp members toward the closed position.

3. A catheter clamp of claim 1, wherein the locking means include a tab movable between a release position and a locking position.

4. A catheter clamp of claim 1, wherein the locking means include a tab extending between said clamp members.

5. A catheter clamp of claim 4, wherein the tab is configured to prop open a clamp member.

6. A catheter clamp of claim 1, wherein the clamp members are U shaped.

7. A catheter clamp of claim 1, wherein the clamp members are C shaped.

8. A catheter clamp of claim 1, wherein the clamp members are arranged generally one on top of the other.

9. A catheter clamp for use with a catheter positionable in a patient, the catheter having a catheter body, the clamp comprising:
    a base adapted to be removably adhered to the patient's skin;
    two clamp members supported on the base and defining a space therebetween to receive the catheter body, the clamp members adapted to move between an open position and a closed position;
    an elongated release tab extending between the two clamp members and configured to pivot about an axis toward and away from the two clamp members to releasably lock the catheter body between the clamp members; and
    a bias member biasing the elongated release tab toward the two clamp members.

10. A clamp of claim 9, wherein the two clamp members are pivotably coupled to each other.

11. A clamp of claim 10, wherein the tab is pivotably attached on one of the clamp members.

12. A clamp of claim 10, wherein the tab has a profile configured to prop open the clamp members.

13. A clamp of claim 10, further comprising a second bias member to bias the clamp members toward the open position.

14. A catheter clamp for use with a catheter positionable in a patient, the catheter having a catheter body, the clamp comprising:
    a base adapted to be removably adhered to the patient's skin;
    two clamp members supported on the base, said clamp members defining a passageway for receiving the catheter body and adapted to move between an open position and a closed position;
    a cam supported on the base and configured to move at least one of the clamp members into the closed position; and
    a lever adapted to enable a user to control movement of the cam.

15. A clamp of claim 14, further comprising an adhesive coating on a bottom surface of the base to enable the clamp to be removably adhered to the patient.

16. A clamp of claim 14, further comprising a bias member that biases one of the clamp members to move into the open position.

17. A clamp of claim 14, wherein one of said clamp members is stationary relative to the base and the other of said clamp members is movable relative to the base.

* * * * *

UNITED STATES PATENT AND TRADEMARK OFFICE
CERTIFICATE OF CORRECTION

| | | |
|---|---|---|
| PATENT NO. | : 7,776,017 B2 | Page 1 of 1 |
| APPLICATION NO. | : 10/940407 | |
| DATED | : August 17, 2010 | |
| INVENTOR(S) | : Dean M. Ponzi et al. | |

It is certified that error appears in the above-identified patent and that said Letters Patent is hereby corrected as shown below:

On the Title Page

(56) References Cited     Delete "correspondhg" Insert -- corresponding --

Other Publications

Signed and Sealed this
Twenty-fourth Day of May, 2011

David J. Kappos
*Director of the United States Patent and Trademark Office*